United States Patent [19]
Chalmers

[11] 3,962,255
[45] June 8, 1976

[54] 1,4-DIAZAEPINE-5-ONES

[75] Inventor: Alexander Michael Chalmers, Cheadle, England

[73] Assignee: Ciba-Geigy Corporation, Ardsley, N.Y.

[22] Filed: July 26, 1974

[21] Appl. No.: 492,087

[30] Foreign Application Priority Data
July 31, 1973 United Kingdom............... 36340/73

[52] U.S. Cl...................... 260/239.3 R; 260/45.8 R
[51] Int. Cl.².......................................... C07D 243/06
[58] Field of Search............................... 260/239.3 R

[56] References Cited
UNITED STATES PATENTS
3,040,029 6/1962 Poppelsdorf et al......... 260/239.3 R

*Primary Examiner*—Henry R. Jiles
*Assistant Examiner*—Robert T. Bond
*Attorney, Agent, or Firm*—Nestor W. Shust

[57] ABSTRACT

According to the present invention, there are provided compounds having the formula:

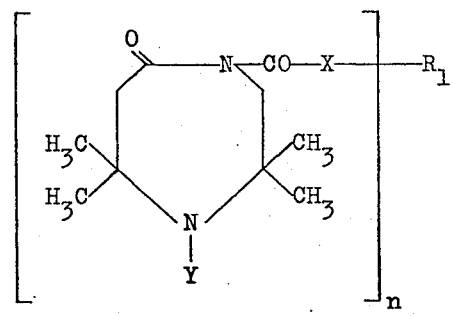

and salts thereof, wherein $n$ is 1 or 2, X is O of NH, Y is O, hydrogen or a branched- or straight chain alkyl residue having from 1 to 4 carbons and $R_1$ is a hydrocarbyl residue having from 1 to 20 carbon atoms, which are useful as stabilisers for polymers.

11 Claims, No Drawings

1,4-DIAZAEPINE-5-ONES

The present invention relates to new N-carbamoyl and N-alkoxycarbonyl diazacycloheptanes useful as stabilisers for polymers.

According to the present invention, there are provided compounds having the formula:

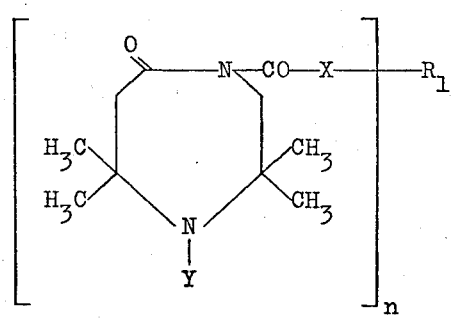

and salts thereof, wherein n is 1 or 2, X is O or NH, Y is O, hydrogen or a branched- or straight chain alkyl residue having from 1 to 4 carbons and $R_1$ is a hydrocarbyl residue having from 1 to 20 carbon atoms.

Examples of Y apart from hydrogen and O, are methyl, ethyl, n-propyl, n-butyl and sec-butyl residues. Particularly preferred values for substituent Y however are hydrogen and methyl residues.

A preferred sub-group of compounds falling within the definition of the compounds of formula I are compounds having the formula:

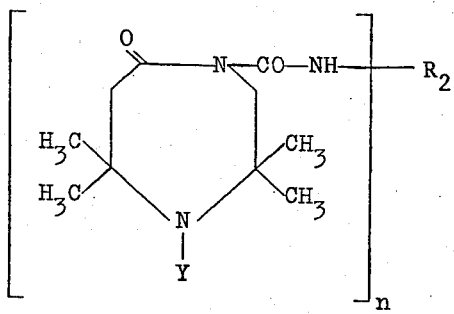

wherein Y and n have their previous significance and, when n is 1, $R_2$ is a branched- or straight- chain alkyl residue having from 1 to 20 carbon atoms, a branched- or straight- chain alkenyl residue having from 3 to 18 carbon atoms, a substituted or unsubstituted cycloalkyl residue having from 5 to 14 carbon atoms, a substituted or unsubstituted aryl residue having from 6 to 12 carbon atoms or an alkaryl residue having from 7 to 18 carbon atoms, and when n is 2, $R_2$ is a branched- or straight- chain alkylene residue having 2 to 20 carbon atoms, an alkenylene residue having 4 to 20 carbon atoms, a substituted or unsubstituted cycloalkylene residue having from 5 to 12 carbon atoms, a substituted or unsubstituted arylene residue having from 6 to 12 carbon atoms, or an alkarylene residue having from 7 to 18 carbon atoms. Substituents on such aromatic residues $R_2$ can be halogen or lower alkoxy groups.

Examples of $R_2$ when n is 1 are methyl, ethyl, n-propyl, isopropyl, n-butyl, sec-butyl, t-butyl, n-pentyl, 2-ethylpentyl, 2-methylpentyl, n-octyl, 2,2,4-trimethylpentyl, n-decyl, n-dodecyl, n-tetradecyl, n-octadecyl, n-eicosyl, allyl, n-decenyl, oleyl, n-octadecenyl, cyclopentyl, cyclohexyl, methylcyclohexyl, t-butylcyclohexyl, t-octylcyclohexyl, cyclododecyl, 1- or 2-perhydronaphthyl, adamantyl, cyclopentylmethyl, cyclohexylmethyl, β-cyclohexylethyl, phenyl, o-, m-, and p-tolyl, 2,4- or 2,6-xylyl, mesityl, p-chlorophenyl, 3-chloro-p-tolyl, o-ethylphenyl, p-t-butylphenyl, 2,3- or 2,5-dichlorophenyl, 2,4- or 2,5-dimethoxyphenyl, α- or β-naphthyl, phenylphenyl or p-n-dodecylphenyl.

Preferred monovalent groups $R_2$ in the N-carbamoyl compounds IA include alkyl residues such as methyl, ethyl, n-propyl, isopropyl, sec-butyl, 2-ethylhexyl, n-dodecyl and n-octadecyl, aryl residues especially phenyl, and alkaryl residues especially those having 7 to 12 carbon atoms.

Examples of $R_2$ when n is 2 are 1,2-ethylene, 1,4-n-butylene, 1,6-n-hexylene, 2,2,4-trimethyl-1,6-n-hexylene, 1,10-n-decylene, 1,20-n-eicosylene, 1,4-n-butenylene, 1,10-n-decenylene, 1,20-n-eicosenylene, 1,3- or 1,4-cyclohexylene, 1,6-cyclododecylene, 3-methylene-3,5,5-trimethyl-cyclohexl-ylene, 1,3- or 1,4-phenylene, 1,5-naphthylene, 4,4'-biphenyl, 2,4-tolylene, 4,4'-diphenylenemethane or 4,4'-diphenylene-1'',6''-n-hexane residues.

Preferred residues $R_2$ when n is 2 are alkylene residues having from 2 to 6 carbon atoms, cycloalkylene residues having from 6 to 12 carbon atoms and alkarylene residues having from 7 to 13 carbon atoms.

A less preferred sub-group of compounds within the definition of compounds of formula I are those having the formula:

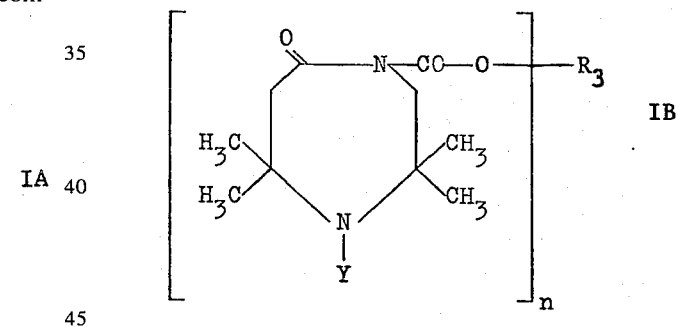

wherein Y and n have their previous significance and when n is 1, $R_3$ is a branched or straight chain alkyl residue having from 1 to 20 carbon atoms or a substituted or unsubstituted aralkyl residue having from 7 to 12 carbon atoms, less preferably, when n is 2, $R_3$ is an alkylene residue having from 2 to 20 carbon atoms or an aralkylene residue having from 8 to 14 carbon atoms. Substituents on such aromatic residues $R_3$ can be halogen, lower alkyl or lower alkoxy groups.

By the term "lower" when used in this specification to describe an alkyl or alkoxy group, we mean those alkyl or alkoxy groups having from 1 to 4 carbon atoms.

Examples of $R_3$ when n is 1 are a methyl, ethyl, n-propyl, isopropyl, n-butyl, sec-butyl, t-butyl, n-pentyl, 2-ethylpentyl, 2-methylpentyl, n-octyl, 2,2,4-trimethylpentyl, n-decyl, n-dodecyl, n-tetradecyl, n-octadecyl, n-eicosyl, benzyl, β-phenylethyl, α-methylbenzyl, p-methylbenzyl or α-naphthylmethyl residue.

Preferred monovalent groups $R_3$ are alkyl residues having from 1 to 10 carbon atoms.

Examples of $R_3$ when n is 2 are 1,2-ethylene, 1,4-n-butylene, 1,6-n-hexylene, 1,10-n-decylene, 1,20-n- eicosylene, p-phenylene bismethylene and 4,4'-dimethylene biphenyl.

Preferred divalent groups $R_3$ are alkylene residues having from 2 to 6 carbon atoms.

Examples of salts of the compounds of formula I include salts of an inorganic acid such as phosphates, carbonates, sulphates, chlorides and the like as well as of an organic acid such as acetates, stearates, maleates, citrates, tartrates, oxalates and benzoates and substituted carbamic acids.

Examples of specific N-substituted carbamoyl and alkoxycarbonyl diazacycloheptanones of formula I are given in the following list:

4-methylcarbamoyl-2,2,7,7-tetramethyl-1,4-diazacycloheptan-5-one
4-ethylcarbamoyl-2,2,7,7-tetramethyl-1,4-diazacycloheptan-5-one
4-n-propylcarbamoyl-2,2,7,7-tetramethyl-1,4-diazacycloheptan-5-one
4-isopropylcarbamoyl-2,2,7,7-tetramethyl-1,4-diazacycloheptan-5-one
4-n-butylcarbamoyl-2,2,7,7-tetramethyl-1,4-diazacycloheptan-5-one
4-n-hexylcarbamoyl-2,2,7,7-tetramethyl-1,4-diazacycloheptan-5-one
4-(2-ethylhexyl)-carbamoyl-2,2,7,7-tetramethyl-1,4-diazacycloheptan-5-one
4-n-dodecylcarbamoyl-2,2,7,7-tetramethyl-1,4-diazacycloheptan-5-one
4-n-eicosylcarbamoyl-2,2,7,7-tetramethyl-1,4-diazacycloheptan-5-one
4-allyl carbamoyl-2,2,7,7-tetramethyl-1,4-diazacycloheptan-5-one
4-n-decenylcarbamoyl-2,2,7,7-tetramethyl-1,4-diazacycloheptan-5-one
4-cyclopentylcarbamoyl-2,2,7,7-tetramethyl-1,4-diazacycloheptan-5-one
4-cyclohexylcarbamoyl-2,2,7,7-tetramethyl-1,4-diazacycloheptan-5-one
4-cyclododecylcarbamoyl-2,2,7,7-tetramethyl-1,4-diazacycloheptan-5-one
4-phenylcarbamoyl-2,2,7,7-tetramethyl-1,4-diazacycloheptan-5-one
4-(2',4'-dimethoxyphenyl)carbamoyl-2,2,7,7-tetramethyl-1,4-diazacycloheptan-5-one
4-p-chlorophenylcarbamoyl-2,2,7,7-tetramethyl-1,4-diazacycloheptan-5-one
4-o-tolylcarbamoyl-2,2,7,7-tetramethyl-1,4-diazacycloheptan-5-one
4-(2',4'-xylyl)carbamoyl-2,2,7,7-tetramethyl-1,4-diazacycloheptan-5-one
4-α-napthylcarbamoyl-2,2,7,7-tetramethyl-1,4-diazacycloheptan-5-one
4-p-t-butylphenylcarbamoyl-2,2,7,7-tetramethyl-1,4-diazacycloheptan-5-one
4-p-n-dodecylphenylcarbamoyl-2,2,7,7-tetramethyl-1,4-diazacycloheptan-5-one
4-methylcarbamoyl-1,2,2,7,7-pentamethyl-1,4-diazacycloheptan-5-one
4-phenylcarbamoyl-1-oxyl-2,2,7,7-tetramethyl-1,4-diazacycloheptan-5-one
4-ethylcarbamoyl-1-n-butyl-2,2,7,7-tetramethyl-1,4-diazacycloheptan-5-one
4-o-tolylcarbamoyl-1-n-propyl-2,2,7,7-tetramethyl-1,4-diazacycloheptan-5-one
4-cyclohexylcarbamoyl-1-sec-butyl-2,2,7,7-tetramethyl-1,4-diazacycloheptan-5-one
4-cycloheptylcarbamoyl-1-isopropyl-2,2,7,7-tetramethyl-1,4-diazacycloheptan-5-one
4-n-hexylcarbamoyl-1-sec-butyl-2,2,7,7-tetramethyl-1,4-diazacycloheptan-5-one
4-n-decylcarbamoyl-1-oxyl-2,2,7,7-tetramethyl-1,4-diazacycloheptan-5-one
4-methoxycarbonyl-2,2,7,7-tetramethyl-1,4-diazacycloheptan-5-one
4-ethoxycarbonyl-2,2,7,7-tetramethyl-1,4-diazacycloheptan-5-one
4-sec-butoxycarbonyl-2,2,7,7-tetramethyl-1,4-diazacycloheptan-5-one
4-n-hexyloxycarbonyl-2,2,7,7-tetramethyl-1,4-diazacycloheptan-5-one
4-n-dodecyloxycarbonyl-2,2,7,7-tetramethyl-1,4-diazacycloheptan-5-one
4-n-eicosyloxycarbonyl-2,2,7,7-tetramethyl-1,4-diazacycloheptan-5-one
4-benzyloxycarbonyl-2,2,7,7-tetramethyl-1,4-diazacycloheptan-5-one
4-β-phenylethoxycarbonyl-2,2,7,7-tetramethyl-1,4-diazacycloheptan-5-one
4-methoxycarbonyl-1-oxyl-2,2,7,7-tetramethyl-1,4-diazacycloheptan-5-one
4-ethoxycarbonyl-1,2,2,7,7-pentamethyl-1,4-diazacycloheptan-5-one
4-isopropoxycarbonyl-1-n-butyl-2,2,7,7-tetramethyl-1,4-diazacycloheptan-5-one
4-sec-butoxycarbonyl-1-oxyl-2,2,7,7-tetramethyl-1,4-diazacycloheptan-5-one
4-n-pentyloxycarbonyl-1-n-propyl-2,2,7,7-tetramethyl-1,4-diazacycloheptan-5-one
4-n-hexyloxycarbonyl-1-isopropyl-2,2,7,7-tetramethyl-1,4-diazacycloheptan-5-one
4-benzyloxycarbonyl-1-ethyl-2,2,7,7-tetramethyl-1,4-diazacycloheptan-5-one
4-β-phenylethoxycarbonyl-1-n-propyl-2,2,7,7-tetramethyl-1,4-diazacycloheptan-5-one
ethane-1',2'-bis[4-carbamoyl-2,2,7,7-tetramethyl-1,4-diazacycloheptan-5-one]
n-hexane-1',6'-bis[4-carbamoyl-2,2,7,7-tetramethyl-1,4-diazacycloheptan-5-one]
2',2',4'-trimethylhexane--1',6'-bis[4-carbamoyl-2,2,7,7-tetramethyl-1,4-diazacycloheptan-5-one]
n-eicosane-1',20'-bis[4-carbamoyl-2,2,7,7-tetramethyl-1,4-diazacycloheptan-5one]
n-eicosene-1',20'-bis[4-carbamoyl-2,2,7,7-tetramethyl-1,4-diazacycloheptan-5-one]
cyclohexane-1',3'-bis[4-carbamoyl-2,2,7,7-tetramethyl-1,4-diazacycloheptan-5-one]
cyclodecane-1',6'-bis[4-carbamoyl-2,2,7,7-tetramethyl-1,4-diazacycloheptan-5-one]
benzene-1',4'-bis[4-carbamoyl-2,2,7,7-tetramethyl-1,4-diazacycloheptan-5-one]
naphthalene-1',5'-bis[4-carbamoyl-2,2,7,7-tetramethyl-1,4-diazacycloheptan-5-one]
toluene-2',4'-bis[4-carbamoyl-2,2,7,7-tetramethyl-1,4-diazacycloheptan-5-one]
diphenylenemethane-4',4''-bis[4-carbamoyl-2,2,7,7-tetramethyl1,4-diazacycloheptan-5-one]
biphenyl-4',4''-bis[4-carbamoyl-2,2,7,7-tetramethyl-1,4-diazacycloheptan-5-one]
[p,p-diphenylenehexane-1',6']-4'',4'''-bis[4-carbamoyl-2,2,7,7-tetramethyl-1,4-diazacycloheptan-5-one]
ethane-1',2'-dioxy-bis[4-carbonyl-2,2,7,7-tetramethyl-1,4-diazacycloheptan-5-one]hexane-1',6'-dioxy-bis[4-carbonyl-1,2,2,7,7-pentamethyl-1,4-diazacycloheptan-5-one]

p-phenylene bis methylenoxy-bis[4-carbonyl-2,2,7,7-tetramethyl-1,4-diazacycloheptan-5-one]

4',4''-dimethyleneoxy biphenyl-bis[4-carbonyl-2,2,7,7-tetramethyl-1,4-diazacycloheptan-5-one]

1-[2',2',7',7'-tetramethyl-5'-oxo-1',4'-diazacycloheptyl-4'-carbonylamino]-3,5,5-trimethyl-3-[2'',2'',7'',7''-tetramethyl-5''-oxo-1'',4''-diazacycloheptyl-4''-carbonylaminomethylene]cyclohexane ethane-1',2'-bis[4-carbamoyl-1-oxyl-2,2,7,7-tetramethyl-1,4-diazacycloheptan-5-one]

n-hexane-1',6'-bis[4-carbamoyl-1-n-butyl-2,2,7,7-tetramethyl-1,4-diazacycloheptan-5-one]

n-butene-1',4'-bis[4-carbamoyl-1-n-propyl-2,2,7,7-tetramethyl-1,4-diazacycloheptan-5-one]

n-eicosane-1'',20'-bis[4-carbamoyl-1-ethyl-2,2,7,7-tetramethyl-1,4-diazacycloheptan-5-one]

cyclohexane-1',3'-bis[4-carbamoyl-1-sec-butyl-2,2,7,7-tetramethyl-1,4-diazacycloheptan-5-one]

cyclopentane-1',3'-bis[4-carbamoyl-1-isobutyl-2,2,7,7-tetramethyl-1,4-diazacycloheptan-5-one]

According to the present invention, there is also provided a process in which there is produced a compound of formula I wherein X is NH comprising reacting a 1,4-diazacycloheptan-5-one having the formula:

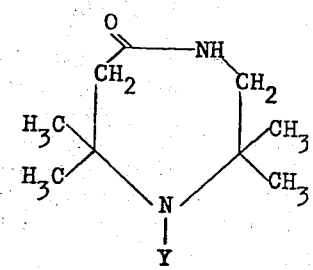

II wherein Y has its previous significance with an isocyanate having the formula:

III wherein $R_1$ and $n$ have their previous significance.

The reaction may be conveniently effected in a solvent which is inert towards the reactants, for instance, benzene, toluene, cyclohexane or dimethylformamide, optionally in the presence of a strong base such as 1,4-diazabicyclo[2.2.2]octane. The reaction may be carried out at the reflux temperature of the mixture, although lower reaction temperature can be used if desired.

The present invention also provides a second, less preferred, process in which a compound of formula I in which X is NH is produced, comprising reacting a compound having the formula II as defined above with phosgene, to produce a compound of the formula:

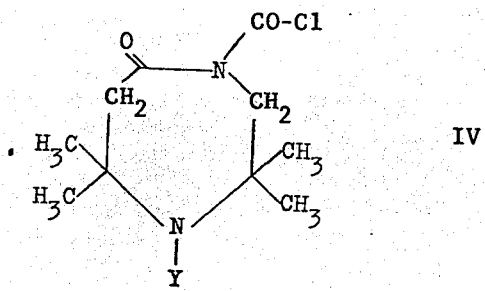

IV wherein Y has its previous significance, which is then reacted with an amine $R_1(NH_2)_n$ wherein $R_1$ and $n$ have their previous significance. Preferably the reaction is effected in a solvent inert towards the reactants.

According to this present invention there is also provided a process of producing a compound of formula I in which X is O and $n$ is 1, comprising reacting a 1,4-diazacycloheptan-5-one of formula II with a chloroformate having the formula:

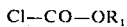

V wherein $R_1$ has its previous significance.

The reaction is conveniently effected in a solvent which is inert towards the reactants, for instance, benzene, toluene or cyclohexane. The reaction is carried out at the reflux temperature of the mixture although a lower temperature can be used if desired. This reaction can also be carried out in the presence of sodium carbonate at the reflux temperature of the mixture or a lower temperature.

According to the present invention there is also provided a second, less preferred, process of producing a compound of formula I (in which X is O) comprising reacting in a solvent inert to the reactants, a compound having the formula IV as hereinbefore defined with an alcohol $R_1OH$ or a diol $HO-R_1-OH$ (or alkali salt thereof) wherein $R_1$ has its previous significance.

The present invention provides a further process for producing a compound of formula I wherein Y is other than hydrogen, comprising reacting the corresponding compound of formula I wherein Y is hydrogen with a commpound capable of replacing the hydrogen at the nitrogen atom by the group Y.

For example, the nitrogen substitution reactions may be effected using an alkylating agent such as an alkyl halide.

Alternatively, the nitrogen substitution reactions may be carried out by a Leuckart or Wallach reaction using formic acid and the appropriate aldehyde or ketone. For example, the corresponding NH compound may be reacted with formic acid and formaldehyde to produce the N-methyl compound.

To produce a compound of formula I wherein Y is O, the corresponding compound of formula I wherein Y is hydrogen may be oxidised with a peroxide, such as hydrogen peroxide, optionally in the presence of pertungstic acid, or with a per-acid such as performic or peracetic acid. In a modification of this oxidation reaction, the starting material may be the corresponding N-lower alkyl compound rather than the NH compound of formula I.

The compounds of formula II are already known and may be prepared according to the method described by Dickermann and Lindwall, J. Org. Chem. 14 530 (1949).

The present invention further provides a composition comprising an organic material and, as stabiliser, a minor proportion of a compound of formula I as hereinbefore defined.

Compounds of formula I have been found to impart to polyolefines an exceptionally high degree of stability towards deterioration normally induced by the effects of ultraviolet radiation or exposure to heat. Moreover, this improved stability is achieved without affecting the colour properties of the treated polyolefine. The stabilisers of the invention provide effective light and/or heat stabilisation especially for low- and high-density polyethylene and polypropylene and polystyrene as well as polymers of butene-1, pentene-1, 3-methylbutene-1, hexene-1, 4-methylpentene-1, 4-methylhexene- 1 and 4,4-dimethylpentene-1, and also co- and terpolymers of olefines, particularly of ethylene or propylene.

Other organic materials susceptible to degradation by the effects of light and the properties of which are improved by the incorporation therein of a compound of formula I include natural and synthetic polymeric materials, for instance natural and synthetic rubbers, the latter including, for example, homo-, co- and terpolymers of acrylonitrile, butadiene and styrene.

Specific synthetic polymers include polyvinyl chloride and vinyl chloride co-polymers, polyvinyl acetate as well as condensation polymers derived from ether, ester (derived from carboxylic, sulphonic or carbonic acids) amide or urethane compounds; polyvinyl acetals; polyacrylates such as polymers and copolymers of methyl acrylate, ethyl acrylate, methyl methacrylate and ethyl methacrylate; polyamide; urea-formaldehyde and malamine-formaldehyde resins; cellulose plastics such as cellulose acetate, cellulose butyrate and cellulose nitrate. Certain of these polymers can, for instance, form the basis of surface coating media such as paints and lacquers having an oil or resin base, such as an alkyd or polyamide resin.

The amount of the compound of formula I which is incorporated into the organic material in order to achieve maximal protection against degradation by light varies according to the properties of the organic material treated and according to the severity of the light radiation and to the length of exposure. However, for most purposes it is sufficient to use an amount of the compound of formula I within the range of from 0.01% to 5% by weight, more preferably within the range of from 0.1% to 2% by weight based on the weight of untreated organic material.

The compounds of formula I may be incorporated into the polymeric material by any of the known techniques for compounding additives with a polymer. For example, the compound of formula I and the polymer may be compounded in an internal mixer. Alternatively, the compound of formula I may be added as a solution or slurry in a suitable solvent or dispersant, for instance an inert organic solvent such as methanol ethanol or acetone to powdered polymer and the whole mixed intimately in a mixer; and the solvent subsequently removed. As a further alternative the compound of formula I may be added to the polymer during the preparation of the latter, for instance at the latex stage of polymer production, to provide pre-stabilised polymer material.

Optionally, the composition of the invention may contain one or more further additives, especially those used in polymer formulations, such as antioxidants of the phenol or amine type, U.V. absorbers and light protectants, phosphite stabilisers, peroxide decomposers, polyamide stabilisers, basic co-stabilisers, polyvinyl chloride stabilisers, nucleation agents, plasticizers, lubricants, emulsifiers, antistatic agents, flame-protectants, pigments, carbon black, asbestos, glass-fibres, kaolin and talc.

The present invention therefore includes binary tertiary and multi-component compositions containing, as stabiliser, a compound of formula I together with one or more functional additives for polymers.

Examples of suitable antioxidants are those of the hindered phenol type such as those selected from the following groups:

1. Phenolic compounds having the general formula

Q—(CH$_2$)$_w$—A$_1$ wherein
Q is

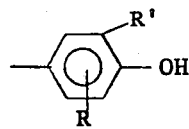

A$_1$ is

—CR(COOR'')$_2$ $$\begin{array}{c} \text{COOR''} \\ | \\ -\text{C}-(\text{CH}_2)_w-\text{Q} \\ | \\ \text{COOR''} \end{array}$$

R is hydrogen or lower alkyl
R' is lower alkyl
R'' is alkyl group having from 6 – 24 carbon atoms
w is an integer from 0 to 4.

Illustrative examples of the compounds shown above are:
di-n-octadecyl-α-(3,5-di-t-butyl-4-hydroxy-benzyl) malonate
di-n-octadecyl-α-(3-t-butyl-4-hydroxy-5-methyl-benzyl) malonate which is disclosed in the Netherlands Pat. No. 6,711,199, Feb. 19, 1968
di-n-octadecyl-αα'bis-(3-t-butyl-4-hydroxy-5-methylbenzyl)malonate which is disclosed in the Netherlands Pat. No. 6,803,498, Sept. 18, 1968.

2. Phenolic compounds having the general formula

Q-R'''

Illustrative examples of the compounds shown above are:
2,6-di-t-butyl-p-cresol
2-methyl-4,6-di-t-butylphenol and the like
2,6-di-Octadecyl-p-cresol 3. Phenolic compounds having the formula Q—C$_n$H$_{2w}$—Q Illustrative examples of the compounds shown are:
2,2'-methylene-bis(6-t-butyl-4-methylphenol)
2,2'-methylene-bis(6-t-butyl-4-ethylphenol)
4,4'-butylidene-bis(2,6-di-t-butylphenol)
4,4'-(2-butylidene)-bis-(2-t-butyl-5-methylphenol)
2,2'-methylene-bis 6-(2-t-methylcyclohexyl)-4-methylphenol
2,2'-methylene-bis(3-t-butyl-5-ethylphenol)
4,4'-methylene-bis(3,5-di-t-butylphenol)
4,4'-methylene-bis(3-t-butyl-5-methylphenol)
2,2'-methylene-bis(3-t-butyl-5-methylphenol)
and the like.

4. Phenolic compounds having the formula:

R'''—O—Q

Illustrative examples of such compounds are:
2,5-di-t-butylhydroquinone
2,6-di-t-butylhydroquinone
2,5-di-t-butyl-4-hydroxyanisole 5. Phenolic compounds having the formula:

Q—S—Q

Illustrative examples of such compounds are:
4,4'-thiobis-(2-t-butyl-5-methylphenol)
4,4'-thiobis-(2-t-butyl-6-methylphenol)
2,2'-thiobis-(6-t-butyl-4-methylphenol)

4,4'-thiobis-(2-methyl-5-t-butylphenol)
6. Phenolic compounds having the formula

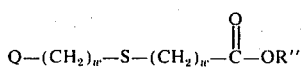

Illustrative examples of such compounds are:
  octadecyl-(3,5-dimethyl-4-hydroxybenzylthio)-acetate
  dodecyl-(3,5-di-t-butyl-4-hydroxybenzylthio)-propionate
7. Phenolic compounds having the formula

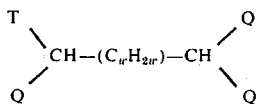

wherein
  T is hydrogen
  R or Q as defined above.
Illustrative examples of such compounds are:
  1,1,3-tris(3,5-dimethyl-4-hydroxyphenyl)propane
  1,1,3-tris(5-t-butyl-4-hydroxy-2-methylphenyl)-butane
  1,1,5,5-tetrakis-(3'-t-butyl-4'-hydroxy-6'-methylphenyl)-n-pentane
8. Phenolic compounds having the formula:

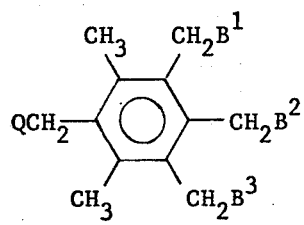

wherein $B^1$, $B^2$ and $B^3$ are hydrogen, methyl or Q, provided that when $B^1$ and $B^3$ are Q then $B^2$ is hydrogen or methyl and when $B^2$ is Q then $B^1$ and $B^3$ are hydrogen or methyl.
Illustrative examples of such compounds are:
  1,4-di(3,5-di-t-butyl-4-hydroxybenzyl)-2,3,5,6-tetramethylbenzene
  1,3,5-tri(3,5-t-butyl-4-hydroxybenzyl)-2,4,6-trimethylbenzene
9. Phenolic compounds having the formula

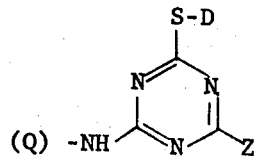

wherein
  Z is NHQ, —S—D— or —O—Q
  D is alkyl group having from 6–12 carbon atoms or $-(C_wH_{2w})-S-R''$
Illustrative examples of such compounds are:
  2,4-bis-(n-octylthio)-6-(3,5-di-t-butyl-4-hydroxyaniline) 1,3,5-triazine
  6-(4-hydroxy-3-methyl-5-t-butylanilino)-2,4-bis-(n-oxtylthio)-1,3,5-triazine
  6-(4-hydroxy-3,5-dimethylanilino)-2,4-bis-(n-octylthio)-1,3,5-triazine
  6-(4-hydroxy-3,5-di-t-butylanilino)-2,4-bis-(n-octylthio)-1,3,5-triazine
  6-(4-hydroxy-3,5-di-t-butylanilino)-4-(4-hydroxy-3,5-di-t-butylphenoxy)-2-(n-octylthio)1,3,5-triazine
  2,4-bis(4-hydroxy-3,5-di-t-butylanilino)-6-(n-octylthio)-1,3,5-triazine
The above phenolic triazine stabilizers are more fully described in U.S. Pat. No. 3,255,191.
10. Phenolic compounds having the formula:

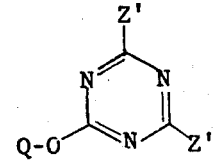

wherein Z' is —O—Q, —S—D or —S—$(C_wH_{2w})$—SD.
Illustrative examples of such compounds are:
  2,3-bis-(3,5-di-t-butyl-4-hydroxyphenoxy)-6-(n-octylthio)-1,3,5-triazine
  2,4,6-tris-(4-hydroxy-3,5-di-t-butylphenoxy)-1,3,5-triazine
  6-(4-hydroxy-3,5-di-t-butylphenoxy)-2,4-bis-(n-octylthioethylthio)-1,3,5-triazine
  6-(4-hydroxy-3-methylphenoxy)-2,4-bis-(n-octylthio)-1,3,5-triazine
  6-(4-hydroxy-3-t-butylphenoxy)-2,4-bis-(n-octylthioethylthio)-1,3,5-triazine
  6-(4-hydroxy-3-methyl-5-t-butylphenoxy)-2,4-bis-(n-octylthio)-1,3,5-triazine
  2,4-bis-(4-hydroxy-3-methyl-5-t-butylphenoxy)-6-(n-octylthio)-1,3,5-triazine
  2,4,6-tris-(4-hydroxy-3-methyl-5-t-butylphenoxy)-1,3,5-triazine
  6-(4-hydroxy-3,5-di-t-butylphenoxy)-2,4-bis-(n-octylthiopropylthio)-1,3,5-triazine
  6-(4-hydroxy-3,5-di-t-butylphenoxy)-2,4-bis-(n-dodecylthioethylthio)-1,3,5-triazine
  2,4-bis-(4-hydroxy-3,5-di-t-butylphenoxy)-6-butylthio1,3,5-triazine
  2,4-bis-(4-hydroxy-3,5-di-t-butylphenoxy)-6-(n-octadecylthio)-1,3,5-triazine
  2,4-bis-(4-hydroxy-3,5-di-t-butylphenoxy)-6-(n-dodecylthio)-1,3,5-triazine
  2,4-bis-(4-hydroxy-3,5-di-t-butylphenoxy)-6-(n-octylthiopropylthio)-1,3,5-triazine
  2,4-bis-(4-hydroxy-3,5-di-t-butylphenoxy)-6-(n-octylthioethylthio)-1,3,5-triazine
  2,4-bis-(4-hydroxy-3,5-di-t-butylphenoxy)-6-(n-dodecylthioethylthio)-1,3,5-triazine.
The above phenolic triazine stabilizers are more fully described in U.S. Pat. No. 3,225,191.
11. Phenolic compounds having the formula

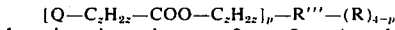

wherein p is an integer from 2 to 4 and R''' is a tetravalent radical selected from aliphatic hydrocarbons having from 1 to 30 carbon atoms, aliphatic mono- and dithioethers having from 1 to 30 carbon atoms, aliphatic mono- and diethers having from 1 to 30 carbon atoms and z is an integer from 0 to 6.
Illustrative examples of such compounds are:

Sub-class I n-Octadecyl-3-(3,5-di-t-butyl-4-hydroxyphenyl)-propionate
n-Octadecyl-2-(3,5-di-t-butyl-4-hydroxyphenyl)-acetate n-Octadcyl-3,5-di-t-butyl-4-hydroxybenzoate
n-Hexyl-3,5-di-t-butyl-4-hydroxyphenylbenzoate
n-Dodecyl-3,5-di-t-butyl-4-hydroxyphenylbenzoate
Neo-dodecyl-3-(3,5-di-t-butyl-4-hydroxyphenyl)-propionate
Dodecyl-β-(3,5-di-t-butyl-4-hydroxyphenyl)-propionate
Ethyl-α-(4-hydroxy-3,5-di-t-butylphenyl)-isobutyrate
Octadecyl-α-(4-hydroxy-3,5-di-t-butylphenyl)-isobutyrate
Octadecyl-α-(4-hydroxy-3,5-di-t-butylphenyl)-propionate

Sub-class II 2-(n-octylthio)ethyl 3,5-di-t-butyl-4-hydroxybenzoate
2-(n-octylthio)ethyl 3,5-di-t-butyl-4-hydroxyphenylacetate
2-(n-octadecylthio)ethyl 3,5-di-t-butyl-4-hydroxyphenylacetate
2-(n-octadecylthio)ethyl 3,5-di-t-butyl-4-hydroxybenzoate
2-(2-hydroxyethylthio)ethyl 3,5-di-t-butyl-4-hydroxybenzoate
2,2'-Thiodiethanol bis(3,5-di-t-butyl-4-hydroxyphenyl)acetate
Diethyl glycol bis-[3,5-di-t-butyl-4-hydroxyphenyl)propionate]
2-(n-octadecylthio)ethyl 3-(3,5-di-t-butyl-4-hydroxyphenyl)propionate
2,2'-Thiodiethanol-bis-3-(3,5-di-t-butyl-4-hydroxyphenyl) propionate
Stearamido N,N-bis-[ethylene 3-(3,5-di-t-butyl-4-hydroxyphenyl)propionate]
n-Butylimino N,N-bis-[ethylene 3-(3,5-di-t-butyl-4-hydroxyphenyl)propionate]
2-(2-stearoyloxyethylthio)ethyl 3,5-di-t-butyl-4-hydroxybenzoate
2-(2-hydroxyethylthio)ethyl 7-(3-methyl-5-t-butyl-4-hydroxyphenyl)heptanoate
2-(2-stearoyloxyethylthio)ethyl 7-(3-methyl-5-t-butyl-4-hydroxyphenyl)heptanoate

Sub-class III 1,2-propylene glycol bis-[3-(3,5-di-t-butyl-4-hydroxyphenyl) propionate]
Ethylene glycol bis-[(3,5-di-t-butyl-4-hydroxyphenyl)propionate]
Neopentylglycol bis-[3-(3,5-di-t-butyl-4-hydroxyphenyl) propionate]
Ethylene glycol bis-(3,5-di-t-butyl-4-hydroxyphenylacetate)
Glycerine-1-n-octadecanoate-2,3-bis-(3,5-di-t-butyl-4-hydroxyphenylacetate
Pentaethylthritol-tetrakis-[3-(3,5-di-t-butyl-4-hydroxyphenyl) propionate]
1,1,1-trimethylol ethane-tris-3-(3,5-di-t-butyl-4-hydroxyphenyl)propionate
Sorbitol hexa-[3-(3,5-di-t-butyl-4-hydroxyphenyl)propionate]
1,2,3-butanetriol tris-[3-(3,5-di-t-butyl-4-hydroxyphenyl) propionate]
2-hydroxyethyl 7-(3-methyl-5-t-butyl-4-hydroxyphenyl)heptanoate
2-stearoyloxyethyl 7-(3-methyl-5-t-butyl-4-hydroxyphenyl)heptanoate
1,6-n-hexanediol-bis[3',5'-di-t-butyl-4-hydroxyphenyl)propionate]

The above phenolic ester stabilizers of sub-classes I, II and III are more fully described in U.S. Pat. No. 3,330,859, Ser. No. 354,464, filed Mar. 24, 1964 and Ser. No. 359,460, filed Apr. 13, 1964, respectively.

12. Phenolic compounds having the formula

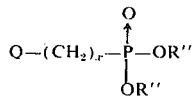

where $x$ is an integer of 1 or 2.

Illustrative examples of such compounds are:
Di-n-octadecyl 3,5-di-t-butyl-4-hydroxybenzyl-phosphonate
Di-n-octadecyl-3-t-butyl-4-hydroxy-5-methylbenzyl-phosphonate
Di-n-octadecyl 1-(3,5-di-t-butyl-4-hydroxyphenyl)ethanephosphonate
Di-n-tetradecyl 3,5-di-t-butyl-4-hydroxybenzyl-phosphonate
Di-n-hexydecyl 3,5-di-t-butyl-4-hydroxybenzyl-phosphonate
Di-n-docosyl-3,5-di-t-butyl-4-hydroxybenzyl-phosphonate
Di-n-octadecyl 3,5-di-t-butyl-4-hydroxybenzyl-phosphonate The above di-(higher)alkyl phenolic phosphonates are more fully described in U.S. Pat. No. 3,281,505.

13. Phenolic compounds having the formula

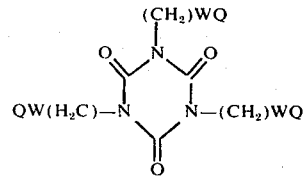

wherein W and Q are defined above.

Illustrative examples of such compounds are:
tris-(3,5-di-t-butyl-4-hydroxybenzyl)isocyanurate
tris-(3-t-butyl-4-hydroxy-5-methylbenzyl)isocyanurate.

The above hydroxyphenylalkenyl isocyanurates are more fully described in U.S. Pat. No. 3,531,483. The above phenolic hydrocarbon stabilizers are known and many are commercially available.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

Further examples of antioxidants are those of the aminoaryl series for instance aniline and naphthylamine derivatives as well as their heterocyclic derivatives such as:-
phenyl-1-naphthylamine
phenyl-2-naphthylamine
N,N'-diphenyl-p-phenyldiamine
N,N'-di-sec.butyl-p-phenylenediamine
6-Ethoxy-2,2,4-trimethyl-1,2-dihydroquinoline
6-Dodecyl-2,2,4-trimethyl-1,2-dihydroquinoline
Mono- and di-octyliminodibenzyl and
polymerised 2,2,4-trimethyl-1,2-dihydroquinoline.

Ultraviolet absorbers and light protectants include:

a. 2-(2'-hydroxyphenyl)benzotriazoles, for instance 5'-methyl; 3',5'-di-t-butyl; 5'-t-butyl; 5-chloro-3', 5'-di-t-butyl; 5-chloro-3'-t-butyl-5'-methyl; 3'-sec. butyl-5'-tert.butyl; 3'-[α-methylbenzyl]-5'-methyl-; 3'-[α-methylbenzyl]-5'-methyl-5-chloro-; 4'-octoxy-; 3',5'-di-t-amyl; 3'-methyl-5'-carbamethoxyethyl; 5-chloro-3',5'-di-t-amyl derivatives.

b. 2,4-bis-(2'-hydroxyphenyl)-6-alkyl-S-triazines, for instance the 6-ethyl or 6-undecyl derivatives.

c. 2-hydroxybenzophenones, for instance the 4-hydroxy, 4-methoxy, 4-octoxy-, 4-decyloxy-, 4-dodecyloxy-, 4,2', 4'-trihydroxy or 2'-hydroxy-4,4'-dimethoxy derivatives.

d. 1,3-Bis(2'-hydroxybenzoyl)-benzenes for instance,
1,3-bis-(2'-hydroxy-4'-hexyloxybenzoyl)benzene
1,3-bis-(2'-hydroxy-4'-octoxybenzoyl)benzene.
1,3-bis-(2'-hydroxy-4'-dodecyloxybenzoyl)benzene e. Aryl esters from optionally substituted benzoic acids such as phenylsalicylate, octylphenylsalicylate, dibenzoyl resorcinol, bis-(4-tert. butylbenzoyl) resorcinol, benzoyl resorcinol and 3,5-di-tert.butyl-4-hydroxybenzoic acid-2,4-di-tert.butyl phenyl ester and -octadecyl ester and -2-methyl-4,6-di-tert.butyl phenyl ester.

f. Acrylates, for instance α-Cyano-β,β-diphenylacrylic acid ethyl- or iso-octyl ester, α-carbomethoxy-cinnamic acid, methyl- or butyl ester and N-(β-carbomethoxyvinyl)-2-methyl indoline.

g. Nickel compounds such as nickel complexes of 2,2'thio-bis-(4-tert.octylphenol), for instance the 1:1 and 1:2 complexes, optionally having other ligands such as n-butylamine, triethanolamine or N-cyclohexyl-diethanolamine; nickel complexes of bis-(4-tert.octylphenyl) sulphone such as the 2:1 complex, optionally having other ligands such as 2-ethylcaproic acid; nickel dibutyl dithiocarbamates; nickel salts of 4-hydroxy-3,5-di-tert.butylbenzyl-phosphonic acid mono-alkyl esters such as the methyl-, ethyl- or butyl esters; the nickel complex of 2-hydroxy-4-methyl-phenyl-undecylketonoxime; and nickel-3,5-di-tert.butyl-4-hydroxy benzoate, and h. Oxalic acid diamides, for instance
4,4'-dioctyloxyoxanilide
2,2'-dioctyloxy-5,5'-di-tert.butyl-oxanilide
2,2'-di-dodecyloxy-5,5'-di-tert.butyl oxanilide
2-ethoxy-5-tertiarybutyl-2'-ethyl-oxanilide
2-ethoxy-2'-ethyl-oxanilide
mixtures of o- and p-methoxy and ethoxy-di-substituted oxanilides and the compound of formula:

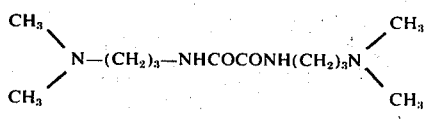

Phosphite stabilisers include triphenyl phosphite, diphenylalkyl phosphites, phenyl dialkyl phosphites, trinonylphenyl phosphite, trilauryl phosphite, trioctadecyl phosphite, 3,9-di-isodecyloxy-2,4,8,10-tetraoxa-3,9-diphosphaspiro-(5,5)-undecane and tri-(4-hydroxy-3,5-di-tert.butylphenyl)phosphite.

Peroxide-decomposing compounds for polyolefins include esters of β-thiodipropionic acids, for instance the lauryl-, stearyl-, myristyl- or tridecyl esters, salts of mercaptobenzimidazoles such as the zinc salt and diphenylthiourea.

Suitable polyamide stabilisers include copper salts in combination with iodides and/or further phosphorus compounds and salts of bivalent manganese.

Basic co-stabilisers are, for example, polyvinylpyrrolidone, melamine, benzoguanamine, triallyl cyanurate, di-cyandiamide, urea derivatives, hydrazine derivatives, amines, polyamides, polyurethanes, alkali and alkaline earth salts of higher saturated or unsaturated fatty acids such as calcium stearate.

Polyvinyl chloride stabilisers include organotin compounds, organo lead compounds and Ba/Cd salts of fatty acids.

Examples of nucleation agents are 4-tert.butyl benzoic acid, adipic acid and diphenylacetic acid.

As with the compound of formula I, any further additive is advantageously employed in a proportion within the range of from 0.01% to 5% by weight, based on the weight of untreated organic materials.

EXAMPLE 1

17 parts of 2,2,7,7-tetramethyl-1,4-diazacycloheptan-5-one and 6.3 parts of methyl isocyanate were heated at reflux for 2 hours in 250 parts of benzene with a catalytic amount of 1,4-diazabicyclo[2.2.2]octane. After evaporation of the solvent in vacuo the product was stirred in 200 parts of water for 18 hours. The aqueous solution was thoroughly extracted with chloroform. Drying and evaporation of the organic phase yielded 20 parts of a colourless solid. Crystallisation from ethyl acetate afforded 4-methylcarbamoyl-2,2,7,7-tetramethyl-1,4-diazacycloheptan-5-one, melting point 147°–149°C which gave the following elemental analysis by weight:

|  | Required for $C_{11}H_{21}N_3O_2$ | Found |
| --- | --- | --- |
| carbon | 58.12% | 58.04% |
| hydrogen | 9.31% | 9.30% |
| nitrogen | 18.49% | 18.79% |

EXAMPLE 2

Using the same conditions as Example 1, 34 parts of 2,2,7,7-tetramethyl-1,4-diazacycloheptan-5-one and 26 parts of phenylisocyanate afforded 49 parts of 4-phenylcarbamoyl-2,2,7,7-tetramethyl-1,4-diazacycloheptan-5-one as an almost colourless solid. Crystallisation from petrol ether (40°–60°) yielded crystalline material of melting point 68.5° – 70°C which gave the following elemental analysis by weight:

|  | Required for $C_{16}H_{23}N_3O_2$ | Found |
| --- | --- | --- |
| carbon | 66.41% | 66.60% |
| hydrogen | 8.01% | 8.03% |
| nitrogen | 14.52% | 14.28% |

EXAMPLE 3

Using similar conditions as in Example 1, 32 parts of 2,2,7,7-tetramethyl-1,4-diazacycloheptan-5-one and 16.8 parts of 1,6-dicyanatohexane afforded 30 parts of hexane-1',6'-bis [4-carbamoyl-2,2,7,7-tetramethyl-1,4-diazacycloheptan-5-one] as a crystalline material. Recrystallisation from petrol ether (40°–60°) yielded a solid of melting point 113°–115°C which gave the following elemental analysis by weight:

| | Required for $C_{26}H_{48}N_6O_4$ | Found |
|---|---|---|
| carbon | 61.39% | 61.16% |
| hydrogen | 9.51% | 9.39% |
| nitrogen | 16.50% | 16.30% |

EXAMPLE 4

Using the same conditions as in Example 1 but with the exception that the reaction time was 16 hours, 10.2 parts of 2,2,7,7,-tetramethyl-1,4-diazacycloheptan-5-one and 8.4 parts of n-hexylisocyanate afforded 17.2 parts of an almost colourless oil, 4-n-hexylcarbamoyl-2,2,7,7-tetramethyl-1,4-diazacycloheptan-5-one. The hydrochloric acid salt of this substance had a melting point of 168°–171°C and gave the following elemental analysis by weight:

| | Required for $C_{16}H_{32}N_3O_2Cl$ | Found |
|---|---|---|
| carbon | 57.55% | 57.25% |
| hydrogen | 9.66% | 9.73% |
| nitrogen | 12.58% | 12.37% |
| chlorine | 10.62% | 10.77% |

EXAMPLE 5

Using the same conditions as in Example 4, 5.1 parts of 2,2,7,7-tetramethyl-1,4-diazacycloheptan-5-one and 3.75 parts of di-(4-isocyanatophenyl)methane afforded an almost colourless solid which was crystallised from ethyl acetate to yield 4′,4″-diphenylmethane-bis[4-carbamoyl-2,2,7,7-tetramethyl-1,4-diazacycloheptan-5-one]. This crystalline solid had a melting point of 164.5°–166°C and gave the following elemental analysis by weight:

| | Required for $C_{35}H_{48}N_6O_4$ | Found |
|---|---|---|
| carbon | 67.08% | 66.75% |
| hydrogen | 7.85% | 8.19% |

EXAMPLE 6

Using the same conditions as in Example 4, 2.76 parts of 1,2,2,7,7-pentamethyl-1,4-diazacycloheptan-5-one and 0.93 parts of methyl isocyanate afforded a colourless solid which was crystallised from petroleum ether (of boiling range 60°–80°C) to give 4-methylcarbamoyl-1,2,2,7,7-pentamethyl-1,4-diazacycloheptan-5-one. This material had a melting point of 111°–113°C and gave the following elemental analysis by weight:

| | Required for $C_{12}H_{23}N_3O_2$ | Found |
|---|---|---|
| carbon | 59.72% | 60.11% |
| hydrogen | 9.61% | 9.34% |
| nitrogen | 17.41% | 17.42% |

EXAMPLE 7

A mixture of 5.1 parts of 2,2,7,7-tetramethyl-1,4-diazaheptan-5-one, 30 parts of ethylchloroformate and 150 parts of anhydrous toluene were heated at reflux for 16 hours. Removal of the solvent under reduced pressure was followed by addition of 10 parts of water to the residue basification with sodium carbonate solution and chloroform extraction. The yellow oil produced was distilled under reduced pressure to yield 4-ethoxycarbonyl-2,2,7,7-tetramethyl-1,4-diazaheptan-5-one of boiling point 98°–100°C at 0.2mm pressure. The hydrochloric acid salt of this material gave the following elemental analysis by weight:

| | Required for $C_{12}H_{23}N_2O_3Cl$ | Found |
|---|---|---|
| carbon | 51.70% | 51.48% |
| hydrogen | 8.31% | 8.14% |
| nitrogen | 10.05% | 10.12% |
| chlorine | 12.71% | 12.67% |

EXAMPLE 8

Using the same conditions as in Example 7, 5.1 parts of 2,2,7,7-tetramethyl-1,4-diazaheptan-5-one, 30 parts of isobutylchloroformate and 150 parts of anhydrous toluene afforded 4-isobutoxycarbonyl-2,2,7,7-tetramethyl-1,4-diazaheptan-5-one of boiling point 134°C at 0.8mm pressure. The hydrochloric acid salt of this material showed a melting point of 179°–181°C and gave the following elemental analysis by weight:

| | Required for $C_{14}H_{27}N_2O_3Cl$ | Found |
|---|---|---|
| carbon | 54.82% | 54.97% |
| hydrogen | 8.87% | 8.75% |
| nitrogen | 9.13% | 8.98% |
| chlorine | 11.55% | 11.75% |

EXAMPLE 9

A mixture of 17 parts of 2,2,7,7-tetramethyl-1,4-diazaheptan-5-one, 19 parts of benzylchloroformate and 250 parts of dry benzene was heated at reflux for 16 hours. The solvent was then evaporated in vacuo to yield an almost colourless oil. Addition of 20 parts of petroleum ether (of boiling range 40° to 60°C) produced 4-benzyloxycarbonyl-2,2,7,7-tetramethyl-1,4-diazacycloheptan-5-one as a colourless solid of melting point 86°–88°C. This material gave the following elemental analysis by weight:

| | Required for $C_{17}H_{24}N_2O_3$ | Found |
|---|---|---|
| carbon | 67.08% | 66.87% |
| hydrogen | 7.95% | 8.14% |
| nitrogen | 9.20% | 9.09 |

EXAMPLE 10

Using the same conditions as in Example 4, 17 parts of 2,2,7,7-tetramethyl-1,4-diazacycloheptan-5-one and 8 parts of ethylisocyanate afforded an almost colourless oil which was distilled in vacuo to yield 20 parts of 4-ethylcarbamoyl-2,2,7,7-tetramethyl-1,4diazacycloheptan-5-one of boiling point 103°–107°C at 1mm pressure. This material gave the following elemental analysis by weight:

| | Required for $C_{12}H_{23}N_3O_2$ | Found |
|---|---|---|
| carbon | 59.72 | 59.36% |
| hydrogen | 9.61% | 9.32% |
| nitrogen | 17.41% | 17.25% |

EXAMPLE 11

Using conditions similar to Example 4, 17 parts of 2,2,7,7-tetramethyl-1,4-diazacycloheptan-5-one and 17 parts of p-chlorophenylisocyanate afforded 20 parts of 4-p-chlorophenylcarbamoyl-2,2,7,7-tetramethyl-1,4-diazacycloheptan-5-one as a colourless solid of melting point 119°–121°C. This material had the following elemental analysis by weight:

|  | Required for $C_{16}H_{22}N_3O_2Cl$ | Found |
|---|---|---|
| carbon | 59.34% | 59.52% |
| hydrogen | 6.85% | 6.91% |
| nitrogen | 12.97% | 13.20% |

EXAMPLE 12

A mixture of 25 parts of 4-n-hexylcarbamoyl-2,2,7,7-tetramethyl-1,4-diazacycloheptan-5-one, 11.2 parts of sodium formate, 25 parts of formaldehyde and 2 parts of formic acid were heated at steam bath temperature for 2 hours. 250 Parts of ammonium hydroxide were then added and the solution extracted with chloroform to yield, after drying, 20 parts of a heavy oil which was further purified by column chromatography (silica) to give pure 4-n-hexylcarbamoyl-1,2,2,7,7-pentamethyl-1,4-diazacycloheptan-5-one. This material had the following elemental analysis by weight:

|  | Required for $C_{17}H_{33}N_3O_2$ | Found |
|---|---|---|
| carbon | 65.56% | 65.26% |
| hydrogen | 10.68% | 10.57% |
| nitrogen | 13.49% | 13.21% |

EXAMPLE 13

Using the same procedure as described in Example 4, 17 parts of 2,2,7,7-tetramethyl-1,4-diazacycloheptan-5-one and 32 parts of n-octadecyl isocyanate were reacted together and afforded 4-n-octadecylcarbamoyl-2,2,7,7-tetramethyl-1,4-diazacycloheptan-5-one as a colourless solid which was recrystallised from petroleum ether (of boiling range 60° to 80°C) and had a melting point of 56.5°–58°C. This material gave the following elemental analysis by weight:

|  | Required for $C_{28}H_{55}N_3O_2$ | Found |
|---|---|---|
| carbon | 72.21% | 72.18% |
| hydrogen | 11.90% | 11.98% |
| nitrogen | 9.02% | 8.79 |

EXAMPLE 14

Using the same procedure as described in Example 4, 17 parts of 2,2,7,7-tetramethyl-1,4-diazacycloheptan-5-one and 14.3 parts of p-tolyl isocyanate were reacted together and afforded a solid material which was recrystallised from petroleum ether (of boiling range 60° to 80°C) to yield 21 parts of 4-p-tolylcarbamoyl-2,2,7,7-tetramethyl-1,4-diazacycloheptan-5-one of melting point 126°C. This material gave the following elemental analysis by weight:

|  | Required for $C_{17}H_{25}N_3O_2$ | Found |
|---|---|---|
| carbon | 67.30% | 67.04% |
| hydrogen | 8.31% | 8.04% |
| nitrogen | 13.85% | 13.57% |

EXAMPLE 15

A mixture of 17 parts of 2,2,7,7-tetramethyl-1,4-diazacycloheptan-5-one, 24 parts of n-decyl chloroformate and 500 parts of dry toluene was heated at reflux for 16 hours. The solvent was then evaporated in vacuo to yield 40 parts of a yellowish liquid which was distilled at 190° to 192°C at 0.2mm pressure to yield pure 4-n-decyloxycarbonyl-2,2,7,7-tetramethyl-1,4-diazacycloheptan-5-one as a colourless liquid. This material gave the following elemental analysis by weight:

|  | Required for $C_{20}H_{38}N_2O_3$ | Found |
|---|---|---|
| carbon | 67.76% | 67.63% |
| hydrogen | 10.80% | 10.51% |
| nitrogen | 7.90% | 7.87% |

EXAMPLE 16

Using the same conditions as in Example 4, 17 parts of 2,2,7,7-tetramethyl-1,4-diazacycloheptan-5-one and 9 parts of allyl isocyanate afforded 26 parts of 4-allylcarbamoyl-2,2,7,7-tetramethyl-1,4-diazacycloheptan-5-one which was purified by distillation at 131°–135°C and 0.3mm pressure. The colourless oil gave the following elemental analysis by weight:

|  | Required for $C_{13}H_{23}N_3O_2$ | Found |
|---|---|---|
| carbon | 61.63% | 61.36% |
| hydrogen | 9.15% | 9.27% |
| nitrogen | 16.59% | 16.34% |

EXAMPLES 17 to 20

38 parts of polypropylene were homogenised with 0.076 parts of n-octadecyl-$\beta$(4'-hydroxy-3',5'-di-t-butylphenyl)propionate in a kneading machine over a period of 3 minutes at 200°C. 0.19 part of the product of Example 7 was then added and homogenisation was continued for another 7 minutes.

This composition was compression moulded into films of 0.1mm thickness at 260°C for 6 minutes and the films so obtained were then quenched in cold water.

A section measuring 44 × 100 mm was separated from the 0.1mm annealed polypropylene foil and exposed in a "Xenotest 150" exposure unit.

The exposed sample was examined periodically and portions of it were tested to determine the percentage elongation at break, the time (T) at which the sample reached 50% of the initial elongation at break being noted.

Similar tests were carried out on polypropylene samples containing, respectively, no stabiliser and the products of Examples, 1, 4 and 12 of the present application. The results obtained are set out in the following table.

| Example | Additive | Factor T/To Time to 50% of initial elongation at break (T) (additive) Time to 50% of initial elongation at break for control (To) |
|---|---|---|
| — | none | 1 |
| 17 | 4-ethoxycarbonyl-2,2,7,7-tetramethyl-1,4- | 3.0 |

-continued

| Example | Additive | Factor T/To Time to 50% of initial elongation at break (T) (additive) Time to 50% of initial elongation at break for control (To) |
|---|---|---|
| 18 | diazaheptan-5-one 4-methylcarbamoyl-2,2,7,7-tetramethyl-1,4-diazacycloheptan-5-one | 8.2 |
| 19 | 4-n-hexylcarbamoyl-2,2,7,7-tetramethyl-1,4-diazacycloheptan-5-one | 6.4 |
| 20 | 4-n-hexylcarbamoyl-1,2,2,7,7-pentamethyl-1,4-diazacycloheptan-5-one | 7.9 |

EXAMPLE 21

Using the same conditions as in Example 4, 3.6 parts of 1-oxyl-2,2,7,7-tetramethyl-1,4-diazacycloheptan-5-one and 2.6 parts of phenyl isocyanate were reacted together and afforded 6.0 parts of a red oil which was purfied by column chromatography on alumina to give 4-phenylcarbamoyl-1-oxyl-2,2,7,7-tetramethyl-1,4-diazacycloheptan-5-one as a red solid of melting point 112° to 114°C. This material gave the following elemental analysis by weight:

| | Required for $C_{16}H_{25}N_3O_3$ | Found |
|---|---|---|
| carbon | 63.13% | 63.22% |
| hydrogen | 7.29% | 7.23% |
| nitrogen | 13.80% | 13.51% |

What we claim is:

1. A compound having the formula:

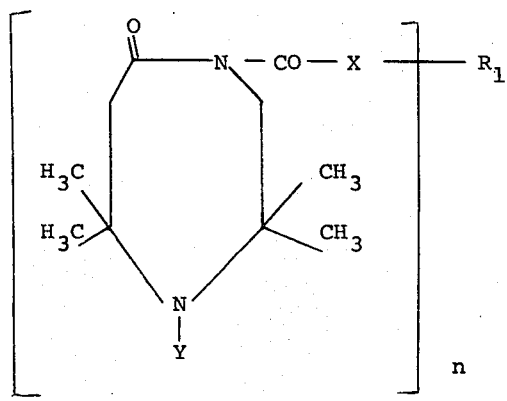

wherein $n$ is 1 or 2, X is O or NH, Y is O, hydrogen or a branched or straight-chain alkyl having from 1 to 4 carbon atoms and $R_1$ is a hydrocarbyl having from 1 to 20 carbon atoms which is selected, when $n$ is 1 from the group consisting of a branched- or straight-chain alkyl having from 1 to 20 carbon atoms, a branched- or straight-chain alkenyl having from 3 to 18 carbon atoms, an unsubstituted cycloalkyl having from 5 to 14 carbon atoms or said cycloalkyl substituted with an alkyl of 1 to 8 carbons unsubstituted aryl selected from phenyl and naphthyl or said aryl substituted with chloro, methoxy or phenyl, an alkaryl having from 7 to 18 carbon atoms said alkyl substituent having 1 to 12 carbons, and when n is 2, from the group consisting of a branched- or straight-chain alkylene having 2 to 20 carbon atoms, an alkenylene having 4 to 20 carbon atoms, an unsubstituted cycloalkylene having from 5 to 12 carbon atoms, a substituted or unsubstituted arylene having from 6 to 12 carbon atoms, or an alkarylene having from 7 to 8 carbon atoms, said aromatic substituents being halogen or lower alkoxy groups; and salts thereof said salts being in the form of a phosphate, carbonate, sulphate, chloride, acetate, stearate, maleate, citrate, tartrate, oxalate, benzoate or carbamate.

2. A compound of claim 1 wherein X is —NH—.
3. A compound of claim 2 in the form of a salt.
4. A compound as claimed in claim 1 wherein Y is hydrogen or methyl.
5. A compound as claimed in claim 2 wherein $n$ is 1 and $R_2$ is a methyl, ethyl, n-propyl, isopropyl, sec-butyl, 2-ethylhexyl, n-dodecyl, n-octadecyl, phenyl or alkaryl having from 7 to 12 carbon atoms.
6. A compound as claimed in claim 2 wherein $n$ is 2 and $R_2$ is an alkylene having from 2 to 6 carbon atoms, a cycloalkylene having from 6 to 12 carbon atoms or an alkarylene having from 7 to 13 carbon atoms.
7. A compound as claimed in claim 1 and having the formula:

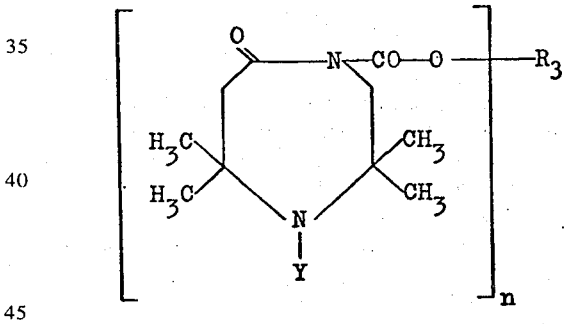

wherein Y and $n$ are as defined in claim 1 and when n is 1, $R_3$ is a branched- or straight-chain alkyl having form 1 to 20 carbon atoms or an aralkyl having from 7 to 12 carbon atoms and being either unsubstituted or substituted with a halogen atom, an alkyl group having from 1 to 4 carbon atoms or an alkoxy group having from 1 to 4 carbon atoms.

8. A compound of claim 7 in the form of a salt.
9. A compound as claimed in clam 7 wherein when $n$ is 2, $R_3$ is an alkylene having from 2 to 20 carbon atoms or an aralkylene having from 8 to 14 carbon atoms.
10. A compound as claimed in claim 7 wherein $R_3$ is an alkyl having from 1 to 10 carbon atoms.
11. A compound as claimed in claim 9 wherein $R_3$ is an alkylene having from 2 to 6 carbon atoms.

* * * * *